US008476468B2

(12) United States Patent
Rauleder et al.

(10) Patent No.: US 8,476,468 B2
(45) Date of Patent: *Jul. 2, 2013

(54) REMOVAL OF EXTRANEOUS METALS FROM SILICON COMPOUNDS BY ADSORPTION AND/OR FILTRATION

(75) Inventors: Hartwig Rauleder, Rheinfelden (DE); Ekkehard Mueh, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/121,702

(22) PCT Filed: Oct. 13, 2009

(86) PCT No.: PCT/EP2009/063316
§ 371 (c)(1),
(2), (4) Date: Mar. 30, 2011

(87) PCT Pub. No.: WO2010/066487
PCT Pub. Date: Jun. 17, 2010

(65) Prior Publication Data
US 2011/0184205 A1    Jul. 28, 2011

(30) Foreign Application Priority Data
Dec. 11, 2008 (DE) .......................... 10 2008 054 537

(51) Int. Cl.
*C07F 7/08* (2006.01)
(52) U.S. Cl.
USPC ............................ 556/479; 556/466; 556/473
(58) Field of Classification Search
None
See application file for complete search history.

(56) References Cited

U.S. PATENT DOCUMENTS

| | | | |
|---|---|---|---|
| 4,224,040 A * | 9/1980 | Gazzarrini et al. | ............. 95/133 |
| 5,616,755 A | 4/1997 | Seiler et al. | |
| 5,698,726 A | 12/1997 | Rauleder et al. | |
| 5,852,206 A | 12/1998 | Horn et al. | |
| 6,142,024 A | 11/2000 | Rauleder et al. | |
| 6,150,551 A | 11/2000 | Kropfgans et al. | |
| 6,680,038 B2 | 1/2004 | Rauleder et al. | |
| 7,204,963 B2 | 4/2007 | Rauleder et al. | |
| 7,410,914 B2 | 8/2008 | Kuehnle et al. | |
| 8,038,961 B2 | 10/2011 | Sonnenschein et al. | |
| 2005/0054211 A1 * | 3/2005 | Xu et al. | ....................... 438/745 |
| 2006/0167296 A1 | 7/2006 | Guennouni et al. | |
| 2008/0197014 A1 | 8/2008 | Lang et al. | |
| 2008/0283972 A1 | 11/2008 | Muh et al. | |
| 2008/0289690 A1 | 11/2008 | Sonnenschein et al. | |
| 2009/0020413 A1 | 1/2009 | Popp et al. | |
| 2010/0266489 A1 | 10/2010 | Rauleder et al. | |
| 2010/0270296 A1 | 10/2010 | Rauleder et al. | |
| 2010/0274028 A1 | 10/2010 | Mueh et al. | |
| 2010/0278706 A1 | 11/2010 | Mueh et al. | |
| 2010/0296994 A1 | 11/2010 | Rauleder et al. | |
| 2010/0320072 A1 | 12/2010 | Schwarz et al. | |
| 2011/0052474 A1 | 3/2011 | Mueh et al. | |

FOREIGN PATENT DOCUMENTS

DE          603 09 058          4/2007

OTHER PUBLICATIONS

International Search Report issued Jan. 18, 2010 in PCT/EP09/063316 filed Oct. 13, 2009.
U.S. Appl. No. 12/999,240, filed Mar. 4, 2011, Seliger, et al.
U.S. Appl. No. 13/059,692, filed Feb. 18, 2011, Lang, et al.
U.S. Appl. No. 13/121,756, filed Mar. 30, 2011, Lang, et al.
U.S. Appl. No. 61/110,827, filed Nov. 3, 2008, Rauleder, et al.
U.S. Appl. No. 13/121,761, filed Mar. 30, 2011, Rauleder, et al.
U.S. Appl. No. 13/121,758, filed Mar. 30, 2011, Lang, et al.
U.S. Appl. No. 61/111,127, filed Nov. 4, 2008, Panz.
U.S. Appl. No. 13/121,754, filed Mar. 30, 2011, Panz, et al.
U.S. Appl. No. 61/111,125, filed Nov. 4, 2008, Panz.
U.S. Appl. No. 13/121,751, filed Mar. 30, 2011, Panz, et al.
U.S. Appl. No. 61/110,828, filed Nov. 3, 2008, Rauleder, et al.
U.S. Appl. No. 13/121,759, filed Mar. 30, 2011, Rauleder, et al.
U.S. Appl. No. 61/112,891, filed Nov. 10, 2008, Lang, et al.
U.S. Appl. No. 13/128,442, filed May 10, 2011, Lang, et al.
U.S. Appl. No. 13/383,965, filed Jan. 13, 2012, Rauleder, et al.
U.S. Appl. No. 13/383,681, filed Jan. 12, 2012, Mueh, et al.
U.S. Appl. No. 13/580,843, filed Aug. 23, 2012, Mueh, et al.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The invention relates to a process for treating a composition containing silicon compounds, especially organosilanes and/or inorganic silanes, and at least one extraneous metal and/or a compound containing extraneous metal, wherein the composition is contacted with at least one adsorbent and/or a first filter and then a composition in which the content of the extraneous metal and/or of the compound containing extraneous metal has been reduced is obtained. The invention further relates to the use of organic resins, activated carbon, silicates and/or zeolites and/or else of at least one filter with small pore sizes to reduce the level of the compounds mentioned.

9 Claims, No Drawings

REMOVAL OF EXTRANEOUS METALS FROM SILICON COMPOUNDS BY ADSORPTION AND/OR FILTRATION

The invention relates to a process for treating a composition containing silicon compounds, especially organosilanes and/or inorganic silanes, and at least one extraneous metal and/or a compound containing extraneous metal, wherein the composition is contacted with at least one adsorbent and/or a first filter and then a composition in which the content of the extraneous metal and/or of the compound containing extraneous metal has been reduced is obtained. The invention further relates to the use of organic resins, activated carbon, silicates and/or zeolites and/or else of at least one filter with small pore sizes to reduce the level of the compounds mentioned.

Especially in the case of use of organic silanes, such as alkoxysilanes, alkylalkoxy-silanes, alkenylalkoxysilanes, alkynylalkoxysilanes, arylalkoxysilanes or else organofunctional silanes and silicic esters in nanotechnology or in the field of microelectronics, there is a need for ultra high-purity silanes in which the typical impurities are reduced down to traces in the region of the detection limit. This is because even small amounts of impurities here have a considerable influence on the quality of the products produced using the silanes. When silicon compounds (organic or inorganic) are used in microelectronics, for example in the deposition of insulating, dielectric or epitactic layers in the semiconductor industry, even traces of contamination with extraneous metal cause considerable problems in these sensitive applications. When extraneous metals are present in the silicon compounds, this leads to undesired doping effects and reduces the lifetime of electronic components as a result of migration processes.

As a result of the process, the industrial scale preparation of organic or inorganic silanes leads to contamination with undesired extraneous metals. These extraneous metals may be present as compounds or else in metallic form.

EP 0 684 245 A2 discloses reducing the content of hydrocarbons in halosilanes by adsorption thereof on an adsorbent, and EP 0 957 105 A2 discloses the reduction of residual halogen contents and the improvement of colour number in alkoxysilane or alkoxysilane-based compositions by a treatment thereof with activated carbon.

It was an object of the present invention to enable a process for reducing the extraneous metal content and also the content of a compound containing extraneous metal in silicon compounds in a simple and economically viable manner. It was a further object to provide ultra high-purity silicon compounds, especially organosilanes and/or inorganic silanes, with ultra low contents of extraneous metals and extraneous metal-containing compounds.

The objects were achieved according to the specifications in the claims. Preferred embodiments are detailed in dependent claims and in the description.

It has been found that, by treating a composition comprising silicon compounds, especially at least one organosilane and/or an inorganic silane, containing at least one extraneous metal and/or a compound containing extraneous metal, with an adsorbent and/or with at least one filter, preferably with two different filters, by contacting it with the latter and then obtaining the composition, the content of extraneous metals and/or of the compounds containing extraneous metal is reduced considerably, especially when the composition is essentially anhydrous before the treatment.

The invention therefore provides a process for treating a composition containing silicon compounds, especially at least one organosilane and/or at least one inorganic silane or a mixture of one of the silanes or of both silanes, and at least one extraneous metal and/or a compound containing extraneous metal, wherein the composition, which is essentially anhydrous especially for inorganic silanes, in a first step, is contacted with at least one adsorbent and/or at least one filter, and optionally, in a further step, contacted with at least one filter, and is preferably filtered, and a composition in which the content of the extraneous metal and/or of the compound containing extraneous metal has been reduced is obtained. More preferably, the steps of contacting with an adsorbent and optionally removing the adsorbent, for example by means of a first filtration, sedimentation, centrifugation, or by flowing the composition through the adsorbent, are combined with an additional filtration step.

In one embodiment, in the process for treating the composition, an adsorbent may simultaneously act as a filter. For example, to this end, the adsorbent may be tightly packed in a cartridge or the like, through which the composition flows. The mean pore size, which is determined in this case in an interparticulate manner by the packing of the adsorbent, may be less than 100 µm, preferably less than 50 µm to 5 µm.

Alternatively, the process for treating the composition can also be effected by filtering the composition; the filter especially has a pore size of less than 100 µm, preferably less than 50 µm to 5 µm; the filter more preferably has a mean pore size between 5 and 30 µm, more preferably from 5 to 10 µm; optionally, in a further step, the composition thus treated can be filtered at least once, the at least one filter having a pore size of less than 5 µm, especially a pore size of less than or equal to 1 µm, more preferably a pore size of less than or equal to 0.1 µm, or else less than or equal to 0.05 µm, and the composition in which the content of the extraneous metal and/or of the compound containing extraneous metal has been reduced is obtained. The pore size can also be determined by the interparticulate packing of an adsorbent.

In the process according to the invention, in the treatment of the composition, the composition in a first step, is contacted with at least one adsorbent, the adsorbent is optionally removed;

for example, the composition may flow through an adsorbent, or be stirred, shaken and/or left to stand with an adsorbent or be contacted with the adsorbent in another manner sufficiently well known to those skilled in the art, the removal can be effected, for example, by a first filtration through a filter; the filter especially has a pore size less than 100 µm, preferably less than 50 µm to greater than 5 µm; the filter more preferably has a mean pore size between 5 and 30 µm, more preferably from 5 to 10 µm; alternatively or additionally, the composition can be centrifuged or sedimented; and in a further step, the composition treated in this way is filtered, the at least one filter having a pore size of less than 5 µm, especially a pore size less than or equal to 1 µm, more preferably a pore size less than or equal to 0.1 µm, or else less than or equal to 0.05 µm the composition in which the content of the extraneous metal and/or of the compound containing extraneous metal has been reduced is obtained.

One filtration step or else more than one filtration step can be effected at standard pressure, elevated pressure or else under reduced pressure at a suitable temperature.

In this context, it is particularly advantageous that the extraneous metal content and/or the content of the compound containing extraneous metal—generally, this is a residual content of extraneous metal or compound containing extraneous metal which is difficult to remove by distillation or cannot be removed any further—especially independently of one another, can be reduced in each case to a content in the range of less than 100 μg/kg, especially less than 50 μg/kg to 0 μg/kg, preferably less than 30 μg/kg to 0 μg/kg, preferentially less than 15 μg/kg to 0 μg/kg, more preferably less than 10 μg/kg to 0 μg/kg, most preferably less than 1 μg/kg to 0 μg/kg.

Organosilanes are considered to be especially organosilanes of the general formula I. The composition for treatment includes at least one organosilane which corresponds to the general formula I

  (I)

where $0 \leq a \leq 3$, $0 \leq b \leq 3$, $0 \leq c \leq 3$ and $a+b+c \leq 3$, $R^1$ is hydrogen, a linear, branched and/or cyclic, optionally substituted alkyl group having 1 to 18 carbon atoms and/or a linear, branched and/or cyclic alkoxy, alkoxyalkyl, aryloxyalkyl, arylalkyl, aminoalkyl, haloalkyl, polyether, polyetheralkyl, alkenyl, alkynyl, epoxyalkyl, ureidoalkyl, mercaptoalkyl, cyanoalkyl, isocyanatoalkyl, methacryloyloxyalkyl and/or acryloyloxyalkyl group having 1 to 18 carbon atoms and/or an aryl group having 6 to 12 carbon atoms, where $R^2$ is hydrogen, a linear, branched and/or cyclic alkyl group having 1 to 18 carbon atoms and/or an aryl group having 6 to 12 carbon atoms, $R^3$ is hydrogen, a linear, branched and/or cyclic alkyl group having 1 to 18 carbon atoms and/or an aryl group having 6 to 12 carbon atoms, and/or $R^4$ is a linear, branched and/or cyclic alkyl and/or alkoxyalkyl group having 1 to 8 carbon atoms, and/or mixtures of these organosilanes.

Inventive organosilanes are especially tetraalkoxysilanes, alkyltrialkoxysilanes and/or dialkyldialkoxysilanes, trialkylalkoxysilanes such as tetraethoxysilane, tetramethoxysilane, methyltriethoxysilane, methyltrimethoxysilane, dimethyldiethoxysilane, dimethyldimethoxysilane, trimethylmethoxysilane and/or trimethylethoxysilane.

In the preferred embodiments, for $R^1$, the aminoalkyl group is preferably selected from the aminopropyl-functional groups of the formulae —$(CH_2)_3$—$NH_2$, —$(CH_2)_3$—NHR', —$(CH_2)_3$—$NH(CH_2)_2$—$NH_2$ or —$(CH_2)_3$—$NH(CH_2)_2$—$NH(CH_2)_2$—$NH_2$, in which R' is a linear, branched or cyclic alkyl group having 1 to 18 carbon atoms or an aryl group having 6 to 12 carbon atoms, the polyether group or the polyetheralkyl group preferably corresponds to one of the formulae R'—(O—$CH_2$—$CH_2$—)$_n$O—$(CH_2)_3$—, R'—(O—$CH_2$—$CH_2$—$CH_2$—)$_n$O—$(CH_2)_3$—, R'—(O—$CH_2$—$CH_2$—$CH_2$—$CH_2$—)$_n$O—$(CH_2)_3$—, R'—(O—$CH_2$—$CH_2$—)$_n$O—, R'—(O—$CH_2$—$CH_2$—$CH_2$—)$_n$O—, R'—(O—$CH_2$—$CH_2$—$CH_2$—$CH_2$—)$_n$O—, R'O[—$CH_2$—CH(CH$_3$)—O]$_n$—$(CH_2)_3$— or R'O[—$CH_2$—CH(CH$_3$)—O]$_n$ with a chain length n equal to 1 to 30, especially 1 to 14, where R' is preferably H or a linear, branched or cyclic alkyl group having 1 to 6 carbon atoms, especially methyl, ethyl, i-propyl or n-propyl, the methacryloyloxyalkyl or the acryloyloxyalkyl groups correspond preferably to a 3-methacryloyloxypropyl group and/or a 3-acryloyloxypropyl group, the alkoxy group is preferably selected from the methoxy, ethoxy, n-propoxy and/or isopropoxy groups, the alkenyl group is preferably a vinyl, isoprenyl or allyl group, the epoxy group preferably corresponds to a 3-glycidyloxypropyl or 2-(3,4-epoxycyclohexyl)ethyl group, the haloalkyl group preferably corresponds to a fluoroalkyl group with an $R^{8*}$—$Y_m$—$(CH_2)_s$— radical where $R^{8*}$ is a mono-, oligo- or perfluorinated alkyl radical having 1 to 9 carbon atoms or a mono-, oligo- or perfluorinated aryl radical, where, in addition, Y corresponds to a $CH_2$, O, aryl or S radical and m=0 or 1 and s=0 or 2. In one embodiment, $R^1$ corresponds to an $F_3C(CF_2)_r(CH_2)_s$ group where r is an integer from 0 to 9, s is 0 or 2, r is preferably 5 and s is preferably 2; particularly preferred groups are the $CF_3(CF_2)_5(CH_2)_2$— or $CF_3(CF_2)_7(CH_2)_2$— or $CF_3(C_6H_4)$— or $C_6F_5$— groups.

In the preferred embodiment, $R^2$ and/or $R^3$ each correspond to hydrogen or a linear or branched alkyl group having 1 to 8 carbon atoms, especially to a methyl, ethyl, n-propyl, isopropyl or n-octyl group or to an aryl group having 6 carbon atoms, and $R^4$ corresponds to a methyl, ethyl, n-propyl or isopropyl group, preference being given overall to tetraalkoxy-, trialkoxy- and/or dialkoxy-substituted silanes.

According to the invention, the compositions are additionally essentially anhydrous. An inventive composition is considered to be anhydrous when the water content according to Karl Fischer is <10 ppm, especially <5 ppm.

In a further preferred embodiment, the composition for treatment comprises organosilanes which correspond to oligomeric or polymeric organosiloxanes which are obtained from the at least partial hydrolysis and condensation of one or more organosilanes of the general formula I

  (I)

where $0 \leq a \leq 3$, $0 \leq b \leq 3$, $0 \leq c \leq 3$ and $a+b+c \leq 3$, $R^1$ is hydrogen, a linear, branched and/or cyclic, optionally substituted alkyl group having 1 to 18 carbon atoms and/or a linear, branched and/or cyclic alkoxy, alkoxyalkyl, aryloxyalkyl, arylalkyl, aminoalkyl, haloalkyl, polyether, polyetheralkyl, alkenyl, alkynyl, epoxyalkyl, ureidoalkyl, mercaptoalkyl, cyanoalkyl, isocyanatoalkyl, methacryloyloxyalkyl and/or acryloyloxyalkyl group having 1 to 18 carbon atoms and/or an aryl group having 6 to 12 carbon atoms, where $R^2$ is hydrogen, a linear, branched and/or cyclic alkyl group having 1 to 18 carbon atoms and/or an aryl group having 6 to 12 carbon atoms, $R^3$ is hydrogen, a linear, branched and/or cyclic alkyl group having 1 to 18 carbon atoms and/or an aryl group having 6 to 12 carbon atoms, and/or $R^4$ is a linear, branched and/or cyclic alkyl and/or alkoxyalkyl group having 1 to 8 carbon atoms, and/or mixtures of these organosilanes. Oligomeric organosiloxanes are considered to be all siloxanes having at least two silicon atoms per siloxane unit.

Particular preference is given to the following substitution patterns for $R^1$, $R^2$, $R^3$ and $R^4$. In the preferred embodiments, for $R^1$, the aminoalkyl group is selected from the aminopropyl-functional groups of the formulae —$(CH_2)_3$—$NH_2$, —$(CH_2)_3$—NHR', —$(CH_2)_3$—$NH(CH_2)_2$—$NH_2$ or —$(CH_2)_3$—$NH(CH_2)_2$—$NH(CH_2)_2$—$NH_2$, in which R' is a linear, branched or cyclic alkyl group having 1 to 18 carbon atoms or an aryl group having 6 to 12 carbon atoms, the polyether group or the polyetheralkyl group preferably corresponds to one of the formulae R'—(O—$CH_2$—$CH_2$—)$_n$O—$(CH_2)_3$—, R'—(O—$CH_2$—$CH_2$—$CH_2$—)$_n$O—$(CH_2)_3$—, R'—(O—$CH_2$—$CH_2$—$CH_2$—$CH_2$—)$_n$O—$(CH_2)_3$—, R'—(O—$CH_2$—$CH_2$—)$_n$O—, R'—(O—$CH_2$—$CH_2$—$CH_2$—)$_n$O—, R'—(O—$CH_2$—$CH_2$—$CH_2$—$CH_2$—)$_n$O—, R'O[—$CH_2$—CH(CH$_3$)—O]$_n$—$(CH_2)_3$— or R'O[—$CH_2$—CH(CH$_3$)—O]$_n$— with a chain length n equal to 1 to 30, especially 1 to 14, where R' is preferably H or a linear, branched or cyclic alkyl group having 1 to 6 carbon atoms, especially methyl, ethyl, i-propyl or n-propyl, the methacryloyloxyalkyl or the acryloyloxyalkyl groups correspond preferably to a 3-methacryloyloxypropyl group and/or a 3-acryloyloxypropyl group, the alkoxy group is preferably selected from the methoxy, ethoxy, n-propoxy and/or isopropoxy groups, the alkenyl group is preferably a vinyl, isoprenyl or allyl group, the epoxy group preferably corresponds to a 3-glycidyloxy-propyl or 2-(3,4-epoxycyclohexyl)ethyl group, the haloalkyl group preferably corresponds to a fluoroalkyl group with an $R^{8*}$—Y, —$(CH_2)_s$— radical where $R^{8*}$ is a mono-, oligo- or perfluorinated alkyl radical having 1 to 9 carbon atoms or a mono-, oligo- or perfluorinated aryl radical, where, in addition, Y corresponds to a $CH_2$, O, aryl or S radical and m=0 or 1 and s=0 or 2. In one embodiment, $R^1$ corresponds to an $F_3C(CF_2)_r(CH_2)_s$ group where r is an integer from 0 to 9, s is 0 or 2, r is preferably 5 and s is preferably 2; particularly preferred groups are the $CF_3(CF_2)_5(CH_2)_2$— or $CF_3(CF_2)_7(CH_2)_2$— or $CF_3(C_6H_4)$— or $C_6F_5$— groups.

The oligomeric or polymeric organosiloxanes comprise especially catenated, cyclic, crosslinked and/or spatially crosslinked structural elements, the catenated and cyclic structural elements in idealized form corresponding to the general formulae II and III

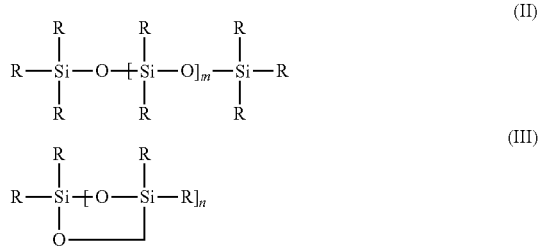

and where, in the crosslinked and/or spatially crosslinked structural elements—which have not been shown in idealized form—the substituents R, like also the substituents R of the structural elements of the formula II and/or III shown in idealized form, consist independently of the organic $R^1$, $R^2$ and/or $R^3$ radicals and/or of hydroxyl groups. In general, the degree of oligomerization may be in the range from 2 to 30, although the degree of oligomerization or polymerization may also be higher. The degree of oligomerization or polymerization of the organosilanes corresponds to the number of silicon units per molecule.

The composition of each oligomeric or polymeric organosiloxane is determined taking account of the fact that each oxygen atom of a monomeric silane unit of the general formula (I) can function as a bridge former between two silicon atoms. Thus, the number of possible available oxygen atoms of each silane of the general formula (I) also determines the functionality of each individual siloxane unit in the organosilane; the monomeric organosilanes of the general formula (I) may thus be present in mono-, di-, tri- or tetrafunctional form.

The structural units present to form oligomeric and/or polymeric organosilanes with catenated, cyclic, crosslinked and/or spatially crosslinked structural elements accordingly include the monofunctional $(R)_3$—Si—O— with the designation M, the difunctional —O—Si(R)$_2$—O— with the designation D, the trifunctional (—O—)$_3$SiR, to which the symbol T has been assigned, and the tetrafunctional Si(—O—)$_4$ with the symbol Q. The structural units are designated according to their functionality with the symbols M, D, T and Q.

Inorganic silanes are understood to mean especially halosilanes, hydrohalosilanes, halosilanes substituted by at least one organic radical and/or hydrohalosilanes substituted by at least one organic radical, and also mixtures of these silanes. In one embodiment, pure hydrosilanes may also be included. In the halogen-containing inorganic silanes, each halogen may be selected independently of further halogen atoms from the group of fluorine, chlorine, bromine and iodine, such that, for example, it is also possible for mixed halosilanes such as $SiBrCl_2F$ or $SiBr_2ClF$ to be present.

The inorganic silanes preferably include the chlorine-substituted, predominantly monomeric silanes, for example tetrachlorosilane, trichlorosilane, dichlorosilane, monochlorosilane, methyltrichlorosilane, trichloromethylsilane, trimethylchlorosilane, dimethyldichlorosilane, phenylmethyldichlorosilane, phenyltrichlorosilane, vinyl-trichlorosilane, dihydrodichlorosilane. However, the extraneous metal content of the monomeric silanes, such as tetramethylsilane, trimethylsilane, dimethylsilane, methylsilane, monosilane or organohydrosilanes, or else disilane, trisilane, tetrasilane and/or pentasilane and higher homologous silanes, can also be reduced by the process according to the invention. In addition to these preferred, predominantly monomeric compounds, it is, however, also possible to correspondingly reduce the extraneous metal content of further dimeric compounds, such as hexachlorodisilane, oligomeric compounds, such as octachlorotrisilane, decachlorotetrasilane, and higher homologous halopolysilanes, and mixed-hydrogenation halogenated polysilanes, for example pentachlorohydrodisilane or tetrachlorodihydrodisilane, and mixtures thereof with monomeric, linear, branched and/or cyclic oligomeric and/or polymeric inorganic silanes. The cyclic oligomeric compounds include compounds of the $Si_nX_{2n}$ type where n>3, such as $Si_5Cl_{10}$, and the polymeric inorganic compounds include, for example, halopolysilanes, i.e. polysilicon halides $Si_nX_{2n+2}$ where n≧5 and/or polysilicon hydrohalides $Si_nH_aX_{[(2n+2)-a]}$ where n≧2 and 0≦a≦(2n+2), where X in each case is a halogen, such as F, Cl, Br, I, especially Cl.

The invention likewise provides a process for treating a composition containing inorganic silanes and at least one extraneous metal and/or a compound containing extraneous metal, according to the above-described process, wherein at least one inorganic silane corresponds to the general formula IV

where 1≦n≦5, 0≦d≦12, 0≦e≦12 and each X in the silane is independently a halogen selected from the group of fluorine, chlorine, bromine and iodine, and each $R^5$ group in the silane is independently a linear, branched and/or cyclic alkyl group having 1 to 16 carbon atoms, or an aryl group. Aryl groups should also be understood to mean alkyl-substituted aryls, with linear, branched or cyclic alkyl groups having 1 to 8 carbon atoms. More preferably, at least one silane corresponds to the general formula IV where n=1, X=chlorine, 0≦d≦3, 0≦e≦3 and d+e≦3 and $R^5$ to a linear, branched and/or cyclic alkyl group having 1 to 16 carbon atoms or an aryl group.

The preferred inorganic silanes include the chlorine-substituted monomeric silanes where n=1 and X=Cl, for example tetrachlorosilane, trichlorosilane, trichloromethylsilane, trimethylchlorosilane, dimethyldichlorosilane, dichlorosilane, monochlorosilane, phenylmethyldichlorosilane, phenyltrichlorosilane, vinyl-trichlorosilane, or else monosilane where d=4 and e=0.

Extraneous metals and/or compounds containing extraneous metal are considered to be those in which the metal does not correspond to silicon. In particular, the at least one extraneous metal and/or the at least one compound containing extraneous metal is/are adsorbed and/or filtered by means of adsorbents and/or filters selectively from the composition containing silicon compounds, such as at least one organosilane and/or an inorganic silane; the adsorption and/or filtration can be effected either in solution or in the gas phase in this case.

Extraneous metals or compounds containing extraneous metals are also understood to mean semimetals or compounds containing semimetals, for example boron, boron trichloride and boric esters such as B(OMe)$_3$ or B(OEt)$_3$, phosphorus (phosphorus trichloride or phosphorus pentachloride, phosphoric esters such as triethyl phosphate), arsenic and antimony and corresponding compounds.

In addition to elemental metals in particulate form, the extraneous metals and/or compounds containing extraneous metal whose levels are to be reduced may be metal halides, metal hydrohalides, metal alkoxides, metal esters and/or metal hydrides and mixtures of these compounds. However, the metal halides, metal hydrohalides or metal halides functionalized with organic radicals such as alkyl or aryl groups can also be removed from organosilanes with very good results. Equally, it is possible, for example, for particulate metals entrained into continuous processes to contaminate the composition. Preferably, the contents of boron, aluminium, potassium, lithium, copper, sodium, magnesium, calcium, iron, chromium, titanium, zinc, vanadium, manganese, cobalt and/or nickel can be reduced; more particularly, compounds based on these metals are removed. More preferably, the content of aluminium, boron and iron; or boron, iron, calcium, copper, potassium and sodium, is reduced.

The process according to the invention is particularly suitable for the removal or reduction of the level of compounds which contain extraneous metal and whose boiling point is in the region of the boiling point of a silicon compound, especially of an organosilane and/or of an inorganic silane, or would be distilled over with the latter as an azeotrope. Portions of these compounds containing extraneous metal can be removed by distillation only with difficulty, if at all. The boiling point within the region of the boiling point of an organosilane and/or inorganic silane is considered to be a boiling point within the range of ±20° C. of the boiling point of one of the silicon compounds or of an organosilane and/or inorganic silane at standard pressure (about 1013.25 hPa or 1013.25 mbar).

In general, the extraneous metal and/or the compound containing extraneous metal can be reduced by 40.0 to 99.8% by weight. In particular, the extraneous metal content is reduced by 50 to 90% by weight, preferably by 65.0 to less than or equal to 100% by weight, preferably by 85 to 95% by weight, more preferably by 95 to 99.8% by weight. This means that, proceeding from the original content, the extraneous metal and/or the compound containing extraneous metal can be removed almost completely from the composition. For iron-containing compositions, the process enables a reduction in the residual content by 85 to 95% by weight, more preferably by 90 to 99.8% by weight, and, according to the combination of the adsorbent and double filtration, by 90 to 99.95% by weight. In general, for example, the aluminium content of a composition of inorganic silanes can be reduced by 40 to 99% by weight, preferably by 85 to 99% by weight, and the boron content by 95 to 99.8% by weight.

The extraneous metal content and/or the content of the compound containing extraneous metal in a composition can preferably be reduced in relation to the metallic compound, especially independently of one another, in each case to a content in the region of less than 100 µg/kg. In the context of the invention, this composition is considered to have ultra high purity. In particular, the content can be reduced to less than 30 µg/kg, preferably less than 15 µg/kg, more preferably less than 10 µg/kg and most preferably less than 1 µg/kg.

To perform the process, it is appropriately possible to use either inorganic or organic adsorbents (synonymous with adsorbers), which may additionally be hydrophilic and/or hydrophobic. According to which extraneous metals or compounds containing extraneous metal are to be removed, it may be appropriate to use a mixture of hydrophilic and hydrophobic adsorbents, or else one adsorbent which has both functions. The adsorbents may be selected from the group of the activated carbons or of the silicates, especially from kieselguhr or siliceous earth; also suitable are zeolites, organic resins or silicates, such as fumed silica and precipitated silica (silica gel). Preferred adsorbents are activated carbon, especially Norit SA+ activated carbon (Norit Deutschland GmbH), Seitz Super kieselguhr (Pall Corporation), kieselguhr (diameter 0.2 to 0.5 mm, Süd-Chemie).

To perform the process, it is appropriately possible to use filter media or filters which are configured, for example, as plate filters or filter plates, as filter cartridges, as filter candles, as depth filters, as filter bags, as drive filters, as membrane filters, as a bed or a suction filter. Preference is given to cartridges. The filters may be based, inter alia, on woven fabrics, fibre-oriented webs, spunbonded webs, random fibre webs or felt—to name just a few examples. For example, it is also possible to use wound filter candles composed of aforementioned materials. In addition, according to the field of use, a wide variety of different materials can be used for filter media useable advantageously, for example cellulose, cellulose fibres, polymers such as nylon, polyester, polyethylene, polypropylene, polyphenylene sulphide, polytetrafluoro-ethylene, PVA, PVDF, synthetic fibres produced therefrom, ceramic fibres/sinter bodies, glass fibres, but also metals, stainless steels, e.g. 316 L, especially in the form of wire, fibres or wool. It is clear to the person skilled in the art that all aforementioned filters of a wide variety of different pore sizes may have a corresponding construction.

In general, the inventive treatment of compositions comprising silicon compounds, such as organosilanes and/or inorganic silanes, is performed in such a way that the adsorbent is first heated in order to carefully dry it and in order to remove any volatile impurities adsorbed and to enable maximum loading of the adsorbent. Subsequently, the dried adsorbent is contacted under protective gas atmosphere with the composition, optionally while stirring. The treatment is suitably effected at room temperature and standard pressure over several hours. The composition is advantageously contacted with the adsorbent for between 1 minute up to 10 hours, especially 2 minutes to 5 hours. The purified composition is generally obtained or removed by filtration, centrifugation or sedimentation. A preferred embodiment consists in using adsorbers (adsorbents) applied to supports, or adsorber mouldings extruded together or fixedly sintered, since the removal of the adsorber material is very much simplified in that case. The supported adsorbents can be used in mouldings familiar to the person skilled in the art, for example as pellets, briquettes, rings or other forms. In a preferred embodiment, a tubular reactor is configured with adsorbent, preferably with supported adsorbent, and the composition can flow through it. This embodiment allows continuous contact with the adsorbent without a downstream additional filtration being necessary in any case. In these configuration variants, the supported adsorbent can also simultaneously fulfil the function of a filter. Overall, however, it is preferred also to connect a fine particulate filter downstream.

In the case of use of pulverulent adsorbers or adsorber granules, the adsorber is preferably removed again, especially by filtration. The filter used is preferably adjusted to the particle size of the adsorbent in order to remove the adsorbent. For this purpose, usually advantageously coarse filter plates are used, which are still permeable at the high loading caused by the adsorber and can be replaced frequently. For example, it is also possible to use belt filters, by means of which the adsorbent can be removed continuously or semicontinuously from the process.

It is common to both process variants that ultrafine, generally unadsorbable metal particles cannot be removed completely. Therefore, in accordance with the invention, a further, very fine particulate filter, especially with a pore size less than 5 μm, is connected downstream, which retains any small to ultra small adsorber particles which break through, with or without adhering extraneous metal and/or compounds containing extraneous metal and particulate metals or particles containing metal. This measure, especially the combined use of adsorbents and downstream filtration, allows the desired purities of <1 ppb per extraneous metal to be achieved. It is possible to use fine particulate filters directly for the removal of a, for example, pulverulent adsorber medium/adsorbent, but this is uneconomical owing to the generally significantly increased costs of these filters.

According to the invention, therefore, a stationary adsorbent, for example in a cartridge, is used, or an adsorbent which is removed from the composition by means of a coarse filtration, which is followed by a downstream filtration with at least one filter with a pore size less than 5 μm.

As required, the process regime may be batchwise, semicontinuous or continuous.

The invention also provides for the use of an organic resin, of an activated carbon, of a silicate and/or of a zeolite for reducing the content of an extraneous metal and/or of at least one compound containing extraneous metal in compositions containing silicon compounds, especially organosilanes and/or inorganic silanes, in particular as defined above particularly preferably in combination with one or more filters, at least one filter having a pore size of less than 5 μm, especially having a pore size of less than 1 μm, more preferably having a pore size of less than or equal to 0.1 μm or else less than or equal to 0.05 μm. Preference is given to using correspondingly supported, sintered or extruded organic resins, activated carbon, silicates and/or zeolites. In preferred embodiments, an adsorbent may be present in stationary form in the manner of a first filter, through which the composition to be purified flows.

The invention also provides for the use of a filter with a pore size of less than 5 μm, especially with a pore size of less than 1 μm, more preferably with a pore size of less than or equal to 0.1 μm or else less than or equal to 0.05 μm, for reducing the content of an extraneous metal and/or of at least one compound containing extraneous metal or of an adsorbent or of particulate impurities in compositions containing silicon compounds, especially organosilanes and/or inorganic silanes, as defined above.

The invention further also provides a composition containing at least one silicon compound as defined above, especially containing at least one organosilane of the formula I or an oligomeric or polymeric organosiloxane derived therefrom by partial hydrolysis and/or condensation, and/or an inorganic silane, especially of the formula IV, wherein the aluminium content <5 μg/kg, in particular <1 μg/kg, the boron content is less than 5 μg/kg, especially less than or equal to 2.5 μg/kg, the iron content is less than 5 μg/kg, especially less than 1 μg/kg, and the calcium, copper, potassium and sodium contents are each less than 1 μg/kg. Moreover, the inventive composition is essentially anhydrous, especially when inorganic silanes are present in the composition.

The inventive composition based on silicon compounds, such as organosilanes and/or inorganic silanes, has an extraneous metal content and/or content of compound containing extraneous metal reduced by 40 to 99.8% by weight. Expressed in μg/kg, the content can be reduced to less than 100 μg/kg, especially less than 30 μg/kg, preferably less than 15 μg/kg, more preferably less than 10 μg/kg, most preferably to less than 1 μg/kg. Particular preference is given to following abovementioned substitution patterns.

With regard to the composition and the structure of the oligomeric and/or polymeric organosilanes, the organosilanes or inorganic silanes, reference is made to the above remarks.

The invention is illustrated in more detail by the examples which follow.

EXAMPLES

Determination of the Boron Content

The samples were prepared and measured in a manner familiar to the analyst skilled in the art, by hydrolysing the sample with demineralized water and treating the hydrolysate with hydrofluoric acid (super pure) to eliminate silicon in the form of volatile silicon tetrafluoride. The residue was taken up in demineralized water and the element content was determined by means of ICP-MS (ELAN 6000 Perkin Elmer).

Example 1

Pretreatment of the Adsorbent

The adsorbent was carefully predried before use, in order to prevent hydrolysis of the silanes to be purified. The drying took place at 110° C. for 3 hours. The adsorbents were stored over desiccants in a desiccator until use.

General Process Method for Treatment of the Silanes:

The silane to be purified was initially charged in a flask with stirrer and nitrogen connection under a nitrogen atmosphere, and a defined amount of the appropriate adsorbent was added. This mixture was subsequently stirred at room temperature for 2 hours, then the adsorbent was removed by means of a pressure filter (Seitz Supradur 100 depth filter, mean pore size 5-10 μm).

The resulting filtrate was subsequently filtered through a particulate filter (Pall Mini Kleen-Change® Filter, material: PTFE, pore size: 0.05 μm, filter area: 320 cm$^2$).

Example 1.1

The example which follows was performed according to the general process method with the amounts specified here.

250 g of tetraethoxysilane with elevated extraneous metal contents were treated with 0.75 g of activated carbon. The extraneous metal contents before and after the treatment and after the particulate filtration were determined by means of ICP-MS; cf. Table 1.1.

TABLE 1.1

Extraneous metal contents before and after the treatment

| Metal | Content before treatment | Content after activated carbon treatment | Content after particulate filtration |
|---|---|---|---|
| Aluminium | 600 μg/kg | 8 μg/kg | <1 μg/kg |
| Boron | 48 μg/kg | 1.4 μg/kg | 1.2 μg/kg |
| Iron | 2970 μg/kg | 9 μg/kg | <1 μg/kg |

Example 1.2

The example which follows was performed according to the general process method with the amounts specified here.

250 g of tetraethoxysilane with elevated extraneous metal contents were treated with 0.75 g of activated carbon in each case. The extraneous metal contents before and after the treatment were determined by means of ICP-MS; cf. Table 1.2.

TABLE 1.2

Extraneous metal contents before and after the treatment

| Metal | Content before treatment | Content after treatment | Content after particulate filtration |
|---|---|---|---|
| Aluminium | 50 µg/kg | 28 µg/kg | <1 µg/kg |
| Boron | 48 µg/kg | 1.2 µg/kg | 1.2 µg/kg |
| Iron | 450 µg/kg | 61 µg/kg | <1 µg/kg |

Example 1.3

The example which follows was performed according to the general process method under Example 1.2 with the amounts specified here.

250 g of methyltriethoxysilane with elevated iron content were treated with 0.75 g of activated carbon. The iron content before and after the treatment was determined by means of ICP-MS; cf. Table 1.3.

TABLE 1.3

Iron content before and after the treatment

| Metal | Content before treatment | Content after treatment | Content after particulate filtration |
|---|---|---|---|
| Iron | 57 µg/kg | 3.1 µg/kg | <1 µg/kg |

Example 2

Tetraethoxysilane was conveyed continuously through a sintered activated carbon element (Pall Schumasorb AC 20, area: 0.11 m$^2$, Ø pore size: 25 µm). A sample of the silane which had been passed through the adsorber candle was filtered through a membrane filter (Anatop™ 25 Plus, Disposable Syringe Filter PLUS Integral Prefilter, pore size 0.1 µm).

The extraneous metal contents before and after the individual treatment steps were determined by means of ICP-MS; cf. Table 2.

TABLE 2

Extraneous metal contents before and after the treatment

| Metal | Content before treatment | Content after activated carbon adsorption | Content after particulate filtration |
|---|---|---|---|
| Boron | 7 µg/kg | 2 µg/kg | 2 µg/kg |
| Iron | 45 µg/kg | 22 µg/kg | 4 µg/kg |
| Calcium | 4 µg/kg | 3 µg/kg | <1 µg/kg |
| Copper | 6 µg/kg | 6 µg/kg | <1 µg/kg |
| Potassium | <1 µg/kg | <1 µg/kg | <1 µg/kg |
| Sodium | 3 µg/kg | 2 µg/kg | <1 µg/kg |

Example 3

119.97 g of Amberlite XAD 4 were initially charged in a 500 ml stirred apparatus consisting of a glass four-neck flask with condenser (water, dry ice), dropping funnel, stirrer, thermometer and nitrogen connection, and dried under reduced pressure (<1 mbar) at approx. 170° C. for 5 hours, dry nitrogen was blown through gently and the mixture was cooled. This was followed by the addition of 250 ml of trichlorosilane via a dropping funnel. The adsorption operation was performed at room temperature and under standard pressure over 5 h. To remove it from the adsorbent, the trichlorosilane was drawn through a glass frit (por. 4, mean pore width 9-15 µm) into an evacuated 500 ml glass flask with outlet device, and, after nitrogen has been blown through it, discharged into a Schott bottle purged with nitrogen.

A sample of the trichlorosilane treated with the adsorbent was filtered through a membrane filter (Arbortech L#942, PTFE membrane, pore size 0.2 µm).

The extraneous metal contents before and after the individual treatment steps were determined by means of ICP-MS; cf. Table 3.

TABLE 3

Extraneous metal content before and after the treatment

| Metal | Content before treatment | Content after adsorption | Content after particulate filtration |
|---|---|---|---|
| Aluminium | 130 µg/kg | 18 µg/kg | <1 µg/kg |
| Boron | 1100 µg/kg | <5 µg/kg | <5 µg/kg |
| Iron | 130 µg/kg | 6 µg/kg | <1 µg/kg |

Example 4

40.01 g of montmorillonite K 10 were initially charged in a 500 ml stirred apparatus consisting of a glass four-neck flask with condenser (water, dry ice), dropping funnel, stirrer, thermometer and nitrogen connection, and dried under reduced pressure (<1 mbar) at approx. 170° C. for 5 hours, dry nitrogen was blown through gently and the mixture was cooled. This was followed by the addition of 250 ml of trichlorosilane via a dropping funnel. The adsorption operation was performed at room temperature and under standard pressure over 5 h. To remove it from the adsorbent, the trichlorosilane was drawn through a glass frit (por. 4, mean pore width 9-15 µm) into an evacuated 500 ml glass flask with outlet device, and, after nitrogen has been blown through it, discharged into a Schott bottle purged with nitrogen.

A sample of the trichlorosilane treated with the adsorbent was filtered through a membrane filter (Arbortech L#942, PTFE membrane, pore size 0.2 µm).

The extraneous metal contents before and after the individual treatment steps were determined by means of ICP-MS; cf. Table 4.

TABLE 4

Extraneous metal content before and after the treatment

| Metal | Content before treatment | Content after adsorption | Content after particulate filtration |
|---|---|---|---|
| Aluminium | 130 µg/kg | <1 µg/kg | <1 µg/kg |
| Boron | 1100 µg/kg | <5 µg/kg | <5 µg/kg |
| Iron | 130 µg/kg | 3.3 µg/kg | <1 µg/kg |

Example 5

20.17 g of Wessalith F 20 were initially charged in a 500 ml stirred apparatus consisting of a glass four-neck flask with condenser (water, dry ice), dropping funnel, stirrer, thermometer and nitrogen connection, and dried under reduced pressure (<1 mbar) at approx. 170° C. for 5 hours, dry nitrogen was blown through gently and the mixture was cooled. This was followed by the addition of 250 ml of trichlorosilane via a dropping funnel. The adsorption operation was performed at room temperature and under standard pressure over 5 h. To remove it from the adsorbent, the trichlorosilane was drawn through a glass frit (por. 4, mean pore width 9-15 µm) into an evacuated 500 ml glass flask with outlet device, and, after nitrogen has been blown through it, discharged into a Schott bottle purged with nitrogen.

A sample of the trichlorosilane treated with the adsorbent was filtered through a membrane filter (Arbortech L#942, PTFE membrane, pore size 0.2 µm).

The extraneous metal contents before and after the individual treatment steps were determined by means of ICP-MS; cf. Table 5.

TABLE 5

Extraneous metal content before and after the treatment

| Metal | Content before treatment | Content after adsorption | Content after particulate filtration |
|---|---|---|---|
| Aluminium | 130 µg/kg | 66 µg/kg | 2.3 µg/kg |
| Boron | 1100 µg/kg | <5 µg/kg | <5 µg/kg |
| Iron | 130 µg/kg | 4.0 µg/kg | <1 µg/kg |

The invention claimed is:

1. A process for purifying a silicon compound, comprising:
    contacting an anhydrous silicon compound comprising at least one metal impurity with a dried adsorbent effective for retention of the metal impurity to adsorb the impurity on the adsorbent;
    removing the adsorbent with the adsorbed impurity from the anhydrous silicon compound to obtain an adsorbent-free anhydrous silicon compound having a reduced content of the impurity; and
    filtering the silicon compound having a reduced content of the impurity through at least one filter having a pore size of 1 µm or less to obtain an ultra-high purity silicon compound;
    wherein
    the silicon compound is an organosilane of formula I, an oligomeric or polymeric organosiloxane which is obtained from at least partial hydrolysis and condensation of at least one organosilane of formula I, or an inorganic silane of formula IV

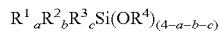  (I), wherein
    $0 \leq a \leq 3$,
    $0 \leq b \leq 3$,
    $0 \leq c \leq 3$,
    $a+b+c \leq 3$,
    $R^1$ is independently hydrogen, a linear, branched, or cyclic, optionally substituted, alkyl group having 1 to 18 carbon atoms, a linear, branched, or cyclic alkoxy, alkoxyalkyl, aryloxyalkyl, arylalkyl, aminoalkyl, haloalkyl, polyether, polyetheralkyl, alkenyl, alkynyl, epoxyalkyl, ureidoalkyl, mercaptoalkyl, cyanoalkyl, isocyanatoalkyl, methacryloyloxyalkyl, or acryloyloxyalkyl group having 1 to 18 carbon atoms or an aryl group having 6 to 12 carbon atoms,
    $R^2$ is independently hydrogen, a linear, branched, or cyclic alkyl group having 1 to 18 carbon atoms or an aryl group having 6 to 12 carbon atoms,
    $R^3$ is independently hydrogen, a linear, branched, or cyclic alkyl group having 1 to 18 carbon atoms or an aryl group having 6 to 12 carbon atoms, and
    $R^4$ is independently a linear, branched, or cyclic alkyl or alkoxyalkyl group having 1 to 8 carbon atoms;

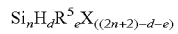  (IV), wherein
    $1 \leq n \leq 5$,
    $0 \leq d \leq 12$,
    $0 \leq e \leq 12$;
    each X is independently a halogen, and
    each $R^5$ group in the silane is independently a linear, branched, or cyclic alkyl group having 1 to 16 carbon atoms, an aryl group, or an alkylaryl group,
    the metal impurity is at least one metal or compound of the metal selected from the group consisting of boron, aluminum, copper, and iron, and
    a content of each metal impurity in the ultra high-purity silicon compound is from 0 µg/kg to 5 µg/kg.

2. The process of claim 1, wherein the silicon compound is an inorganic silane of formula (IV) and the inorganic silane is at least one selected from the group consisting of a monosilane, a monochlorosilane, a dichlorosilane, a trichlorosilane, a tetrachlorosilane, methyltrichlorosilane, dimethyldichlorosilane, and trimethylchlorosilane.

3. The process of claim 1, wherein the metal impurity is a metal compound, which is at least one selected from the group consisting of a metal halide, a metal hydride, a metal hydrohalide, a metal oxide, a metal ester, a metal halide substituted by at least one organic radical, and a metal hydride substituted by at least one organic radical.

4. The process of claim 1, wherein the the pore size of the at least one filter is less than or equal to 0.1 µm.

5. The process of claim 1, wherein the metal impurity is a metal and the metal is at least one selected from the group consisting of aluminum, boron, iron, and copper.

6. The process according to claim 1, wherein
    the adsorbent effective for retention of the impurity is in a physical form selected from the group consisting of a pulverulant powder, a granule, a pellet, a briquette and a ring, and
    the removal of the purified silicon compound from the adsorbent comprises a coarse filtration.

7. The process according to claim 1, wherein a boiling point of the metal impurity differs from a boiling point of the silicon compound by 20° C. or less.

8. A process for purifying a silicon compound, comprising:
    placing an anhydrous silicon compound comprising at least one metal impurity into a filter comprising a dried adsorbent effective for retention of the impurity;
    passing the anhydrous silicon compound through the adsorbent and the filter to obtain a purified anhydrous silicon compound having a reduced content of the at least one metal impurity; and
    filtering the purified silicon compound through at least one filter having a pore size of 1 µm or less to obtain an ultra-high purity silicon compound;
    wherein
    the silicon compound is an organosilane of formula I, an oligomeric or polymeric organosiloxane which is obtained from at least partial hydrolysis and condensation of at least one organosilane of formula I, or an inorganic silane of formula IV

  (I), wherein
- $0 \leq a \leq 3$,
- $0 \leq b \leq 3$,
- $0 \leq c \leq 3$,
- $a+b+c \leq 3$,
- $R^1$ is independently hydrogen, a linear, branched, or cyclic, optionally substituted, alkyl group having 1 to 18 carbon atoms, a linear, branched, or cyclic alkoxy, alkoxyalkyl, aryloxyalkyl, arylalkyl, aminoalkyl, haloalkyl, polyether, polyetheralkyl, alkenyl, alkynyl, epoxyalkyl, ureidoalkyl, mercaptoalkyl, cyanoalkyl, isocyanatoalkyl, methacryloyloxyalkyl, or acryloyloxyalkyl group having 1 to 18 carbon atoms or an aryl group having 6 to 12 carbon atoms,
- $R^2$ is independently hydrogen, a linear, branched, or cyclic alkyl group having 1 to 18 carbon atoms or an aryl group having 6 to 12 carbon atoms,
- $R^3$ is independently hydrogen, a linear, branched, or cyclic alkyl group having 1 to 18 carbon atoms or an aryl group having 6 to 12 carbon atoms, and
- $R^4$ is independently a linear, branched, or cyclic alkyl or alkoxyalkyl group having 1 to 8 carbon atoms;

$$Si_n H_d R^5_e X_{((2n+2)-d-e)} \quad (IV),$$

wherein
- $1 \leq n \leq 5$,
- $0 \leq d \leq 12$,
- $0 \leq e \leq 12$;
- each X is independently a halogen, and
- each $R^5$ group in the silane is independently a linear, branched, or cyclic alkyl group having 1 to 16 carbon atoms, an aryl group, or an alkylaryl group,
- the metal impurity is at least one metal or compound of the metal selected from the group consisting of boron, aluminum, copper, and iron, and
- a content of each metal impurity in the ultra high-purity silicon compound is from 0 μg/kg to 5 μg/kg.

9. The process according to claim 8, wherein the filter comprising a dried adsorbent effective for retention of the impurity is a cartridge filter.

\* \* \* \* \*